United States Patent [19]

Blankenstein et al.

[11] Patent Number: 6,039,941
[45] Date of Patent: Mar. 21, 2000

[54] LIVE VACCINE FOR THE TREATMENT OF TUMOR DISEASES

[75] Inventors: Thomas Blankenstein; Sophie Cayeux-Pezzutto, both of Berlin, Germany

[73] Assignee: Max-Delbrück-Centrum Für Molekulare Medizin, Berlin, Germany

[21] Appl. No.: 08/793,104

[22] PCT Filed: Aug. 18, 1995

[86] PCT No.: PCT/DE95/01164

§ 371 Date: May 20, 1997

§ 102(e) Date: May 20, 1997

[87] PCT Pub. No.: WO96/05866

PCT Pub. Date: Feb. 29, 1996

[30] Foreign Application Priority Data

Aug. 24, 1994 [DE] Germany .............................. 44 31 401

[51] Int. Cl.$^7$ .......................... A01N 63/00; A61K 48/00; C12N 15/63; C12N 15/85

[52] U.S. Cl. ........................ 424/93.21; 424/93.7; 514/44; 435/320.1; 435/325

[58] Field of Search .......................... 514/44; 424/93.21, 424/93.7; 435/320.1, 325

[56] References Cited

FOREIGN PATENT DOCUMENTS

WO
A9321959  11/1993  European Pat. Off. .

OTHER PUBLICATIONS

A. Porgador et al., Natural Immunity, "Immunotherapy of Tumor Metastasis Via Gene Therapy", Mar. 1994 & May 1994, pp. 113–130, vol. 13, Nr 2–3.

R. Costello et al., Immunology, "Interleukin–7 is a Potent Co–stimulus of the Adhesion Pathway Involving CD2 and CD28 Molecules", Nov. 1993, pp. 451–457, vol. 80, Nr. 3.

L. Chen et al., Cell, "Immunotheraphy of Tumor Metastasis Via Gene Therapy", Dec. 24, 1992, pp. 1093–1102, vol. 71.

A. Belldegrun et al. Journal of the National Cancer Institute, "Human Renal Carcinoma Line Transfected With Interleukin–2 and/or Interferon Alpha Gene(s): Implications for Live Cancer Vaccines", Feb. 3, 1993 pp. 207–216, vol. 85, Nr 3.

D. Pardoll, Current Opinion in Immunology, "New Strategies for Active Immunotherapy with Genetically Engineered Tumor Cells", Dec. 1992, pp. 619–623, vol. 4, Nr. 6.

S. Cayeux et al. European Journal of Immunology, "Tumor Cells Co–transfected with Interleukin–7 and B7.1 Genes Induce CD25 and CD28 on Tumor–infiltrating T Lymphocytes and are Strong Vaccines", Aug. 1995, pp. 2325–2331, vol. 25, Nr. 8.

S. Cayeux et al., Immunobiology, "Analysis of the Vaccination–efficiency of Cytokine/B7–transfected Tumor Cells", Sep. 1994, pp. 208–209, vol. 191, Nr. 2–3.

*Primary Examiner*—Paula K. Hutzell
*Assistant Examiner*—Geetha P. Bansal
*Attorney, Agent, or Firm*—Nikaido Marmelstein Murray & Oram, LLP

[57] ABSTRACT

The invention concerns the preparation and use of a live tumour-cell vaccine which contains three additional genes prepared by genetic-engineering techniques: a) a gene coding for a cell-surface protein with immunostimulatory activity, b) a cytokin gene and c) the thymidine kinase gene. The fields of application of the invention are medicine and genetic engineering. The live vaccine proposed owes its effect to the fact that a synergistic anti-tumour response is induced by the multiple transfer of genes which code for immunostimulatory activity. This leads to reliable repulsion of the vaccine cells and enables cells capable of multiplying to be injected as a vaccine. As an additional safety marker, the vaccine cells are given the thymidine kinase gene which enables the vaccine cells to be selectively killed in vivo. The combinatory expression of genes with immunostimulatory activity improves the vaccine effect in comparison with prior art tumour-cell vaccines, and a live tumour-cell vaccine is more effective than a vaccine consisting of cells which are incapable of multiplying. The vaccine is intended for use in the genetic therapy of cancer patients.

17 Claims, 1 Drawing Sheet

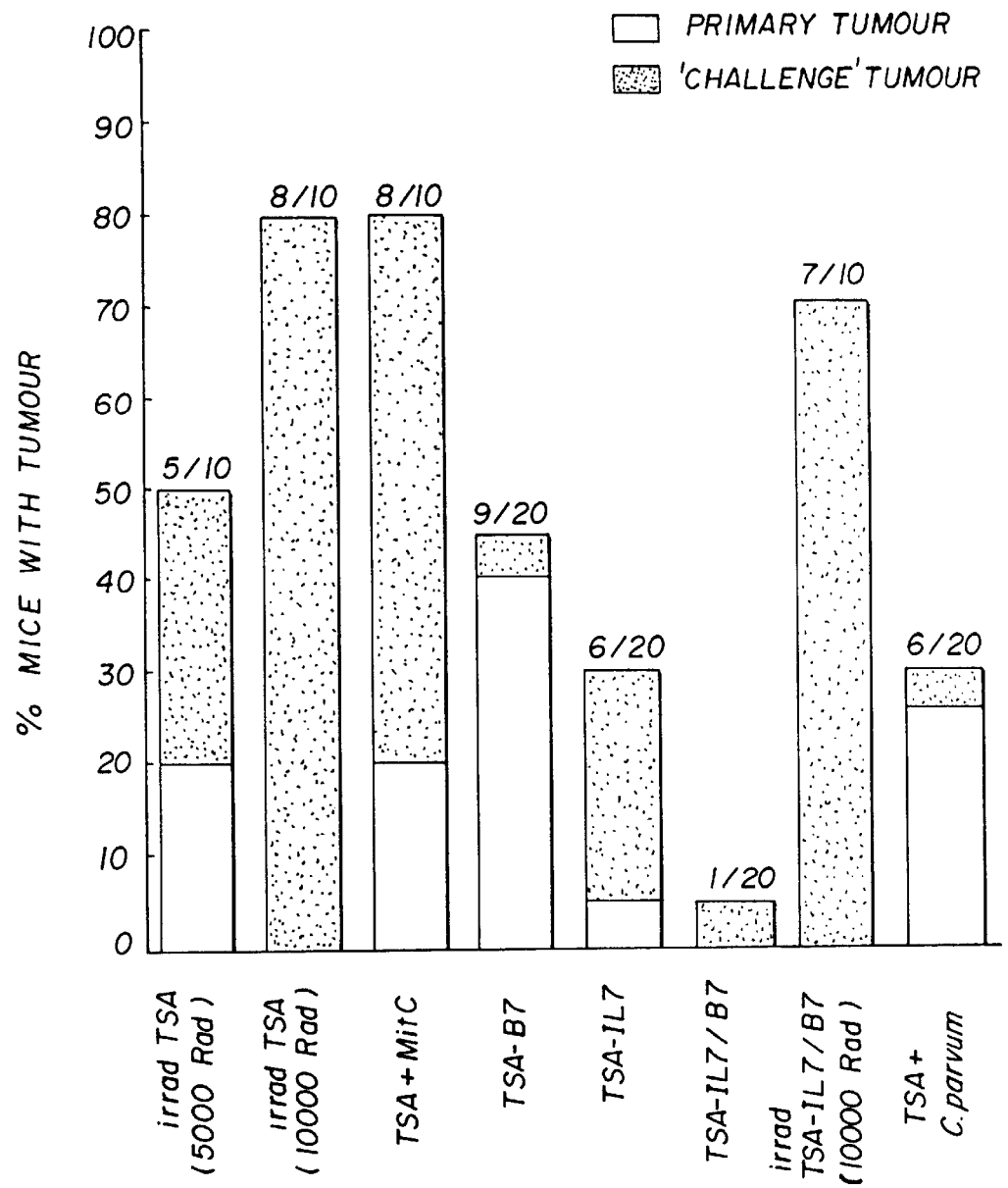

LIVE VACCINE FOR THE TREATMENT OF TUMOR DISEASES

DESCRIPTION

The invention concerns a live vaccine against tumour diseases, its production and its use. Fields of application are medicine and genetic engineering.

Vaccines against tumour diseases have been known for a long time. The classical vaccines that have been used very often clinically are composed of a mixture of irradiated tumour cells and adjuvants such as for example lysates of Bacillus Calmette-Guerin (BCG) or Corynebacterium parvum. After two decades of clinical evaluation it may be summarized that these vaccines do not have a reproducible effect (cf review article: Oettgen, H. and Old, L., The History of Cancer Immunotherapy, in: Biological Therapy of Cancer, Eds. V. deVita, S. Hellman and S. Rosenberg, J. B. Lippincott Company 1991, p. 87–119). Recent results from animal models have shown that the transfer and expression of some cytokine genes (e.g. IL2, IL4, IL7, TNF, IFNγ) can suppress the growth of gene-modified tumour cells in vivo but not in vitro. This inhibition of the tumour growth is the result of an immune response induced by the transfected cytokine. In many cases the gene-transfected tumour is completely rejected (cf. review article: Blankenstein, Eur. J. Cancer, 1994, in press). In a similar manner the expression of the B7 molecule a cell surface protein with costimulatory activity for T-lymphocytes, can inhibit tumour growth. However, the therapeutically important question is whether the rejection of the gene-transfected tumour leads to a long-term persistent immunological memory for the tumour cells. This would be recognized by the fact that animals that had rejected the gene-transfected tumour could later also reject tumour cells that had not been administered by gene transfection. This is also the case to a limited extent and at present several clinical studies are being carried out based on this finding in which irradiated tumour cells provided with a single cytokine gene are being used as vaccines (cf review article: Tepper, R. and Mule, J., 1994 Hum. Gene Therapy 5, 153–164). These studies are referred to as gene therapy studies.

A virus-modified, tumour-specific vaccine is described in DE-OS 38 06 565 which is composed of tumour cells from an operation preparation of a patient who was to be treated later which have been inactivated by irradiation and with NDV virus under sterile conditions. The application of this vaccine was improved according to DE-OS 39 22 444 by using it together with systemically administered cytokines and optionally with haematopoesis-stimulating factors and/ or antisuppressive agents.

A disadvantage of the previously used vaccines is their low effectivity. This assertion is based on the one hand on one of the earlier findings that have shown that the vaccine effect of a tumour cell transfected with a single cytokine gene is no better than that which can be achieved by a tumour cell/adjuvant mixture (Hock et al., 1993, Cancer Res. 53, 714–716). As mentioned above tumour cell/ adjuvant mixtures have been shown clinically to be not effective. On the other hand neither the expression of a single cytokine nor the expression of the B7 molecule alone leads to a reliable rejection of the tumour. I.e. a certain percentage of the mice which have been injected with gene transfected cells develop a tumour after a latency period which is often associated with loss of the cytokine production (Hock et al., 1993, PNAS 90, 2774–2778). This prohibits tumour cells which have been transfected with a single gene coding for immuno-stimulatory activity from being used as live tumour cell vaccines.

The object of the invention is to eliminate the disadvantages of the known vaccines i.e. their inadequate effectiveness together with the necessity of having to inject tumour cells that are incapable of proliferation. It is intended to develop a live vaccine by genetic engineering which stimulates the immune system towards tumour cells that are already in the body.

This object is achieved by a vaccine according to claim 1; the subclaims are preferred variants.

It is produced in autologous or allogeneic systems as claimed in claim 12 and it is used as claimed in claims 13 to 15.

The live vaccine according to the invention for the treatment of tumour diseases with gene-modified tumour cells comprises a cytokine gene and an immunostimulatory membrane protein gene. Autologous or allogeneic tumour cells capable of proliferation are used which can additionally contain one or several suicide genes.

Cytokines are understood as substances which induce the differentiation, proliferation and activation of immune cells. According to the invention the live vaccine can comprise the gene for interleukin-2, interleukin-4, interleukin-7, interferon or granulocyte macrophage colony stimulating factor (GM-CSF) as the cytokine gene; immunostimulatory membrane protein genes are proteins which activate T cells in particular the gene for the T cell costimulatory molecule B7.

Suicide genes are substances which convert the active substances into a toxic product; the thymidine kinase gene of the herpes simplex virus (HSV-TK gene) or the cytosine deaminase gene is particularly preferred.

The live vaccine is used as a therapeutic agent especially for the treatment of tumour diseases.

The starting point for the vaccine can be any desired tumour cell (autologous or allogeneic). Three therapeutic genes are introduced into this cell; this gene transfer can be by any desired method (e.g. retroviral gene transfer). Each of the three therapeutic genes is coupled to a promoter (e.g. Moloney murine leukaemia virus long terminal repeat, elongation factor 1, cytomegalovirus) which acts constitutively. All three genes integrate stably and at random into the genome of the tumour cell. The three therapeutic genes can be optionally present on one or distributed over two vectors. The successful gene transfer is established by positive selection markers (e.g. neomycin gene, hygromycin gene) that are additionally present on the vectors.

The first gene is a cytokine gene (e.g. IL4, IL7). Most cytokines have numerous functions and induce differentiation, proliferation and activation of various immune cells. The local secretion of the transfected cytokine gene by the tumour cells in vivo leads to an inflammatory reaction and an activation of the immune cells (among others T lymphocytes) against the tumour. The result is the rejection of the tumour in most but not in all cases. Only some of the animals which have rejected the tumour transfected with the cytokine gene are immune towards the tumour. The second gene codes for a cell surface protein with immunostimulatory activity (e.g. B7). B7 is usually expressed on antigen-presenting cells and serves, via interaction with its ligands CD28 or CTLA-4, as a co-stimulatory signal for the activation of T lymphocytes. In the absence of B7 T lymphocytes stimulated via the T cell receptor are driven into a state of anergy. Tumour cells transfected with the B7 gene stimulate in vivo a T cell-mediated immune response which, however, only sometimes leads to a rejection of the tumour and results in a moderate vaccine effect. The third gene is a so-called suicide gene (e.g. the thymidine kinase gene of the herpes simplex virus, HSV-TK). The HSV-TK can convert the non-toxic Gancyclovir into a toxic product. This allows tumour cells expressing HSV-TK to be selectively killed by systemic Gancyclovir administration without damaging normal tissue. The HSV-TK gene serves as an additional safety marker to switch off the live tumour cell vaccine.

The tumour cell vaccine according to the invention produced by genetic engineering loses its effectiveness if cells that are incapable of proliferation are used (e.g. by irradiation or mitomycin C treatment). In vaccines that have previously been tested on humans the tumour cells have been irradiated since the growing out of the vaccine cells as a tumour represented a risk to safety. In contrast to tumour cells transfected with a single gene, double gene transfer of a cytokine gene and the B7 gene leads to a 100% tumour rejection. This surprising synergistic effect of two genes which code for immunostimulatory activity that can be achieved by the invention enables the use of a live cell vaccine which can be additionally safeguarded by the option of activating the HSV-TK gene by Gancyclovir. A further distinguishing feature of the vaccine is that due to the cytokine and B7 gene transfer it acquires a higher effectiveness compared to cells that have only been transfected with one of the two genes. It is intended to elucidate the invention in more detail by the following examples of application.

APPLICATION EXAMPLE

1. Expression of cytokine, B7 and HSV-TK genes in tumour cells cDNAs for cytokine, B7 and HSV-TK genes can be isolated by the polymerase chain reaction using suitable primers and cloned into appropriate (retroviral) vectors. Retroviruses are produced with the aid of known packaging cell lines (Pa317, Psi2) and mouse tumour cells are infected with these (plasmacytoma J558L and mammaadeno carcinoma TSA). The successful gene transfer is ensured by selection markers (neomycin gene, hygromycin gene) which are located on the vectors. The expression of the cytokine genes is detected by commercially available ELISAs or a biological assay. IL4 can for example be determined by the IL4-dependent proliferation of CT.4S cells, IL7 by IL7-dependent proliferation of the cell line IXN. B7 expression is determined by staining the tumour cells with a fluorescent-labelled anti-B7 antibody. The expression of the HSV-TK gene is checked by adding Gancyclovir (1–10 µg/ml) to the culture medium for a period of 10–14 days and determining the death of the tumour cells. Cell lines are produced which express either only IL4/IL7 or B7 or both genes together. The cells additionally contain the HSV-TK gene.

2. Rejection of the tumour cell vaccine by IL4/IL7 and B7

Four million J558L, J558-IL4, J558-B7, J558-IL4/B7 and 1 million TSA, TSA-IL7, TSA-B7 and TSA-IL7/B7 tumour cells are injected subcutaneously into 6–8 week old syngenic BALB/c mice and the tumour growth is monitored over a time period of at least 6 months. Non-gene transfected or mock-transfected tumour cells grow in all cases as a tumour. Between 17.6 and 65% of the mice which had only received tumour cells transfected with a single gene also develop a tumour. In neither of the two tumour models (J558L and TSA) were IL4/IL7 and B7-cotransfected tumour cells capable of growing as a tumour, not even in a single case. A total of 100 mice were analysed. The results are summarized in Table 1.

TABLE 1

Rejection of gene-modified tumour cells in BALB/c mice

| Injected tumour cells | Number of mice with tumour/ mice in the experiment | in % |
| --- | --- | --- |
| J558L | 20/20 | 100 |
| J558-IL4 | 6/34 | 17.6 |
| J558-B7 | 14/59 | 23.7 |
| J558-IL4/B7 | 0/80 | 0 |
| TSA | 20/20 | 100 |
| TSA-IL7 | 6/20 | 30 |
| TSA-B7 | 13/20 | 65 |
| TSA-IL7/B7 | 0/20 | 0 |

3. Rejection of the tumour cell vaccine by Gancyclovir

Since tumour cells transfected with the cytokine/B7-gene are reliably rejected, the HSV-TK gene marker was tested as safety marker in TSA cells that had only been labelled with the HSV-TK gene. One million TSA or TSA-TK cells were injected subcutaneously into BALB/c mice. One day later the mice were treated intraperitoneally for a time period of 5 days with 150 mg/kg body weight Gancyclovir or saline. The Gancyclovir treatment had no influence on the tumour growth of parental TSA cells (10/10 mice with tumour), TSA-TK cells grew as a tumour in non-treated mice (10/10 mice with tumour) but were eliminated in most cases in Gancyclovir-treated mice (2/10 mice with tumour). Thus the HSV-TK gene already acts alone as a safety marker and together with the synergistic cytokine/B7 effect described above should ensure a reliable switching off of the live tumour cell vaccine.

4. Effectiveness of the gene-modified tumour cell vaccine

BALB/c mice were immunized subcutaneously with 4 million cells. There were groups immunized with J558L, J558-IL4, J558-B7, J558-IL4/B7 cells and one group immunized with J558L/C parvum adjuvant. With the exception of the J558L cells which had been made incapable of proliferation by irradiation, all cells were injected live. After three weeks the mice were injected contralaterally with 4 million parental tumour cells (challenge tumour) and the tumour growth was monitored. The result as shown in Table 2 shows that the vaccine effect of the J558-IL4/B7 cells was larger than that of the J558-IL4 or J558-B7 cells or the tumour cell/adjuvant mixture.

TABLE 2

Vaccine effect of the gene-modified tumour cell vaccine

| Vaccine cells | Mice with challenge tumour/ mice in the experiment | in % |
| --- | --- | --- |
| none | 20/20 | 100 |
| J558L, irradiated | 20/20 | 100 |
| J558-IL4 | 12/28 | 43 |
| J558-B7 | 18/48 | 38 |
| J558-IL4/B7 | 11/50 | 22 |
| J558/adjuvant | | |

5. Vaccine effect of live compared to irradiated tumour cells

All tumour cell vaccines that have previously been used on patients have been used in an irradiated form for reasons of safety since tumour cells transfected with a single gene or tumour cells mixed with an adjuvant often grow as a tumour. The finding that the three-fold gene-transfected tumour cells described above are reliably rejected enables them to be used as a live vaccine. As a result the effectiveness of the vaccine is increased. If namely BALB/c mice are immunized with 4 million live or irradiated J558-IL4/B7 cells and injected contralaterally three weeks later with 4 million parental J558 cells, 60% (6/10) of the mice immunized with irradiated cells develop a tumour but 0% (0/10) of the mice immunized with living cells develop a tumour.

6. Vaccination effectiveness

The vaccination effectiveness of cells that coexpress IL-7/B7.1 is higher than cells transfected with only one individual gene and higher than a tumour cell/adjuvant (C. parvum) mixture.

In order to compare the vaccination strength of IL-7/B7.1 cotransfected TSA cells with that of the clinically extensively tested adjuvant C. parvum or with non-proliferating TSA cells, groups of mice were immunized with $2.5 \times 10^5$ viable TSA-IL7, TSA-B7.1, TSA-IL7/B7.1 or original cells mixed with C. parvum.

Additionally mice were immunized with irradiated (5000 or 10000 rad) TSA or TSA-IL7/B7.1 cells or TSA cells which had been treated with mitomycin C (60 $\mu$/ml). As a countercheck tumour-free mice were injected two weeks later with at another site with $2.5 \times 10^5$ non-modified cells ('challenge' tumour). FIG. 1 shows the frequency of tumours and namely those which grow out of vaccine cells and those which grow out of the parental cells administered later. The tumour growth of the vaccine cells was only prevented in all mice when the cells had been irradiated with 10000 rad or when cells cotransfected with IL-7/B7 had been used for the immunization. 80% (8/10) of the mice that had been immunized with parental cells irradiated with 10000 rad and 30% (3/10) of the mice which had been immunized with parental cells irradiated with 5000 rad developed a tumour from the parental cells administered later. In the latter group 20% (2/10) developed a tumour from the vaccine cells. In an analogous manner 80% (8/10) of the mice which had been immunized with TSA cells treated with mitomycin C developed a tumour (20% primary tumour, 60% 'challenge' tumour). In the tumour cell/C. parvum group 25% (5/20) of the mice developed a tumour from the vaccine cells and 5% (1/20) from the challenge cells. Of those mice which had rejected the TSA-B7.1 vaccine cells (60%, 12/20), 5% (1/20) developed a 'challenge' tumour. In contrast the mice pretreated with TSA-IL7 developed a 'challenge' tumour in 25% of the cases (5/20) and 5% (1/20) developed a tumour from the vaccine cells. In other words B7 expressed by the tumour cells led to a comparatively poor tumour rejection but a good vaccine effect whereas IL-7 resulted in an improved rejection of the vaccine cells but to a poorer vaccine effect. B7.1 and IL-7 therefore activate the immune system in a different and complementary manner. Since only TSA-IL-7/B7.1 vaccine cells were completely rejected in all mice and protected against tumour growth of the parental cells that were administered later in 19/20 (95%) of the mice, IL-7 and B7 act in a synergistic manner.

All of the above mentioned immunization experiments with transfected tumour cells were carried out with live cells. In addition the vaccination effect of live TSA-IL-7/B7 cells which had been used for the immunization was compared with that of the same cells which had been irradiated with 10000 rad prior to injection. 95% (19/20) of the mice which had been immunized with live cells but only 30% (3/10) of the mice which had been immunized with irradiated cells were able to reject the 'challenge' tumour (FIG. 1). Therefore the effectiveness of the described vaccine is due to the synergistic effect of IL-7 and B7 and the use of cells that are capable of proliferation.

7. Phenotypic description of T lymphocytes in transfected tumours and the growth of tumour cell lines in naked and SCID mice In order to investigate the cellular mechanism of the IL-7/B7.1-induced tumour rejection, an immunofluorescent analysis of the tumour-infiltrating T cells was carried out. For this parental TSA cells, TSA-IL7 cells, TSA-B7.1 cells and TSA-IL7/B7.1 cells were injected subcutaneously into Balb c mice and after 6, 8, and 10 days the tumour nodules were isolated, single cell suspensions were prepared and cells were stained using immunofluorescence with mAbs against CD4, CD8, CD25 and CD28. The percentages of $CD4^+$ and $CD8^+$ cells among the infiltrating cells are shown in Table 3 whereas the percentages of $CD4^+$ and $CD8^+$ cells which are coexpressed with $CD28^+$ and $CD25^+$ (p55 IL2 receptor) are shown in Table 4. $CD4^+$ and $CD8^+$ T cells were both multiplied in TSA-B7 compared to the parental tumours. In TSA-IL7 tumours an increase of $CD4^+$ T cells was observed. T cells ($CD4^+$ and $CD8^+$) were not further increased in IL7/B7 transfected tumours. However, the double fluorescent staining for the T cell subtype marker CD4 and CD8 as well as the activation markers CD28 and CD25 revealed phenotypically different T cells in IL7 or B7 transfected tumours. In TSA-B7 tumours a high percentage of the T cells ($CD4^+$ and $CD8^+$) are $CD28^+$ but most T cells are $CD25^-$. In contrast the T cells in TSA-IL7 tumours are mainly $CD25^+$ and $CD28^-$ cells are essentially absent. As a comparison only a few $CD28^+$ and almost no $CD25^+$ T cells were detected in parental tumours. It is important that in TSA-IL7/B7 tumours most $CD4^+$ and $CD8^+$ cells are $CD25^+$ and $CD28^+$. Taken in connection with the fact that only IL7/B7 cotransfected cells were reliably rejected and induced a very strong systemic tumour immunity (see above), the local IL-7 secretion and B7 expression by the tumour cells is particularly suitable for activating the lymphocytes infiltrating the tumour. In order to demonstrate that the concerted tumour suppression activity of IL7 and B7 is solely due to T cells, TSA cells transfected with IL-7, B7, IL-7/B7 and in comparison TSA cells transfected parentally or with a control vector were injected into naked and SCID mice and the tumour growth kinetics were compared. As can be seen in Table 5 neither the IL-7 secretion nor the B7 expression by tumour cells nor both together are able to delay tumour growth in one of the immuno-deficient mice strains which proves that T cells are absolutely necessary for the IL-7 and B7 induced antitumour immune response.

TABLE 3

Percentages of $CD4^+$ and $CD8^+$ cells among the tumour infiltrating cells

| Tumour cell line | % positive cells* | |
|---|---|---|
| | $CD4^+$ | $CD8^+$ |
| TSA | 15.7 +/− 4.0 | 9.7 +/− 5.0 |
| TSA-B7.1 | 46.3 +/− 2.1 | 24.0 +/− 3.6 |
| TSA-IL7 | 30.0 +/− 7.2 | 10.0 +/− 1.7 |
| TSA-IL7/B7.1 | 28.6 +/− 4.0 | 14.3 +/− 9.3 |

TABLE 4

Percentages of CD4+ and CD8+ cells which expressed the CD28+ and CD25+ marker

| Tumour cell line | % CD4+ cells* | | % CD8+ cells* | |
|---|---|---|---|---|
| | CD28+ | CD25+ | CD28+ | CD25+ |
| TSA | 14.3 +/− 6.0 | 0.0 +/− 0.0 | 14.0 +/− 12.0 | 0.0 +/− 0.0 |
| TSA-B7.1 | 48.0 +/− 20.2 | 13.7 +/− 3.5 | 65.3 +/− 37.8 | 22.0 +/− 11.0 |
| TSA-IL7 | 7.6 +/− 0.6 | 39.0 +/− 7.5 | 4.3 +/− 7.5 | 56.3 +/− 31.5 |
| TSA-IL7/B7.1 | 67.0 +/− 21.6 | 55.3 +/− 25.0 | 67.6 +/− 28.0 | 67.7 +/− 15.6 |

*Tumour infiltrated cells were stained with mAbs using immunofluorescence. For each experiment 5 mice were injected with 2.5 × 10⁵ of the respective cells and the tumours were isolated after 8 days. 3 independent experiments were carried out for each group. +/− SD denotes standard deviation.

TABLE 5

Analysis of the tumour growth of TSA tumour cell lines in immuno-deficient mice

| Tumour cell lines | nu/nu | SCID |
|---|---|---|
| TSA | 5/5 (19 +/− 2) | 5/5 (20 +/− 2) |
| TSA-TK | 5/5 (19 +/− 1) | 5/5 (20 +/− 1) |
| TSA-B7.1 | 5/5 (21 +/− 2) | 5/5 (20 +/− 1) |
| TSA-IL7 | 5/5 (22 +/− 3) | 5/5 (22 +/− 1) |
| TSA-IL7/B7.1 | 5/5 (22 +/− 0) | 5/5 (21 +/− 1) |

The said cells (2.5×10⁵) were injected subcutaneously into the mice strains. The tumour incidence and tumour latency (in brackets) are stated.

We claim:

1. A therapeutic agent comprising live tumor cells which have been genetically modified to comprise:
   a) an operon comprising a cytokine gene and sequences necessary for its expression, and
   b) an operon comprising an immunostimulatory membrane protein gene and sequences necessary for its expression, wherein the genetically modified tumor cells are autologous or allogeneic tumor cells capable of proliferation. wherein the cytokine gene codes for a substance which induces the differentiation, proliferation and activation of immune cells, and wherein the immunostimulatory membrane protein gene codes for a membrane protein that stimulates T cells.

2. The therapeutic agent of claim 1 further comprising an operon with a suicide gene and sequences necessary for its expression.

3. The therapeutic agent of claim 2, wherein the suicide gene codes for an enzyme which can convert a non-toxic compound into a toxic product.

4. The therapeutic agent of claim 3, wherein the suicide gene is selected from the group consisting of the thymidine kinase gene of herpes simplex virus and cytosine deaminase gene.

5. The therapeutic agent of claim 1, wherein the cytokine is selected from the group consisting of interleukin 2, interleukin 4, interleukin 7, interferon and granulocyte macrophage colony stimulation factor (GM-CSF).

6. The therapeutic agent of claim 1, wherein the immunostimulatory membrane protein gene is the gene of the T cell costimulatory molecule B7.

7. The therapeutic agent of claim 1, wherein one or more of the sequences necessary for the expression of the cytokine gene and the immunostimulatory membrane protein gene causes constitutive expression.

8. A pharmaceutical composition comprising the therapeutic agent of claim 1 and a pharmaceutically acceptable excipient.

9. A method of treating a tumor comprising administering to a subject in need of such treatment, a tumor treating effective amount of the therapeutic agent of claim 1.

10. A method of treating a tumor comprising administering to a subject in need of such treatment, a tumor testing effective amount of the therapeutic agent of claim 1, wherein the genetically modified tumor cells are from the same tumor type as the tumor to be treated.

11. A method of making a therapeutic agent comprising live tumor cells which have been genetically modified to comprise: a) an operon comprising a cytokine gene and sequences necessary for its expression, and b) an operon comprising an immunostimulatory membrane protein gene and sequences necessary for its expression, said method comprising:
   a) obtaining autologous or allogenic tumor cells; and
   b) introducing into said tumor cells at least two additional genes wherein said additional genes are a cytokine gene and an immunostimulatory membrane protein gene, wherein the cytokine gene codes for a substance which induces the differentiation, proliferation and activation of immune cells, and wherein the immunostimulatory membrane protein gene codes for a membrane protein that stimulates T cells.

12. The method of claim 11 further comprising a step of:
   c) selecting the tumor cells which have acquired said at least two additional genes after step b).

13. The method of claim 11 wherein a suicide gene is also introduced into said tumor cells.

14. A therapeutic agent comprising live tumor cells which have been genetically modified to comprise:
   a) an operon comprising a cytokine gene and sequences necessary for its expression, and
   b) an operon comprising an immunostimulatory membrane protein gene and sequences necessary for its expression, wherein the genetically modified tumor cells are autologous or allogeneic tumor cells capable of proliferation, wherein the cytokine is IL-4 or IL-7, and wherein the immunostimulatory membrane protein gene is the gene for T cell costimulatory molecule B7.

15. The therapeutic agent of claim 14, further comprising an operon with a suicide gene and sequences necessary for its expression.

16. A pharmaceutical composition comprising the therapeutic agent of claim 14 and a pharmaceutically acceptable excipient.

17. A method of treating tumor diseases comprising administering to a subject, in need of such a treatment, a tumor treating effective amount of the therapeutic agent of claim 14.

* * * * *